United States Patent [19]

Mason, Jr. et al.

[11] 4,296,746

[45] Oct. 27, 1981

[54] DISPOSABLE FULL-FACE SURGICAL MASK

[75] Inventors: Stanley I. Mason, Jr., Weston; Michael D. Handler, Ridgefield, both of Conn.

[73] Assignee: Surgikos, New Brunswick, N.J.

[21] Appl. No.: 104,948

[22] Filed: Dec. 18, 1979

[51] Int. Cl.³ ............................................. A62B 7/10
[52] U.S. Cl. ....................... 128/201.15; 128/201.12; 128/206.12; 128/206.24
[58] Field of Search .................. 128/201.12, 201.15, 128/139, 201.23, 201.25, 206.24, 206.28, 206.21, 206.12, 206.15, 206.11, 206.17; 2/9

[56] References Cited

U.S. PATENT DOCUMENTS

| | | | |
|---|---|---|---|
| 1,324,747 | 12/1919 | Runyan | 128/206.24 |
| 2,355,283 | 8/1944 | Diss | 128/201.23 X |
| 2,665,686 | 1/1954 | Wood et al. | 128/206.24 X |
| 3,152,588 | 10/1964 | Rogowski | 128/206.12 |
| 3,563,236 | 2/1971 | Hansson | 128/201.15 |

FOREIGN PATENT DOCUMENTS

| | | | |
|---|---|---|---|
| 647559 | 7/1937 | Fed. Rep. of Germany | 128/206.24 |
| 556664 | 10/1972 | Switzerland | 128/139 |
| 8457 | 11/1907 | United Kingdom | 128/206.24 |

*Primary Examiner*—Henry J. Recla

[57] ABSTRACT

A lightweight, disposable face mask for covering the entire face of the wearer, which mask comprises a unitary shell of transparent plastic material having upper and lower portions joined at a ridge which traces the facial respiratory line. A band of flexible material is disposed along the ridge and creates an aerodynamic seal between the upper and lower portions of the mask when worn. A strip of soft, flexible material is secured to the mask along the periphery creating a soft, comfortable seal between the mask and the face of the wearer.

11 Claims, 10 Drawing Figures

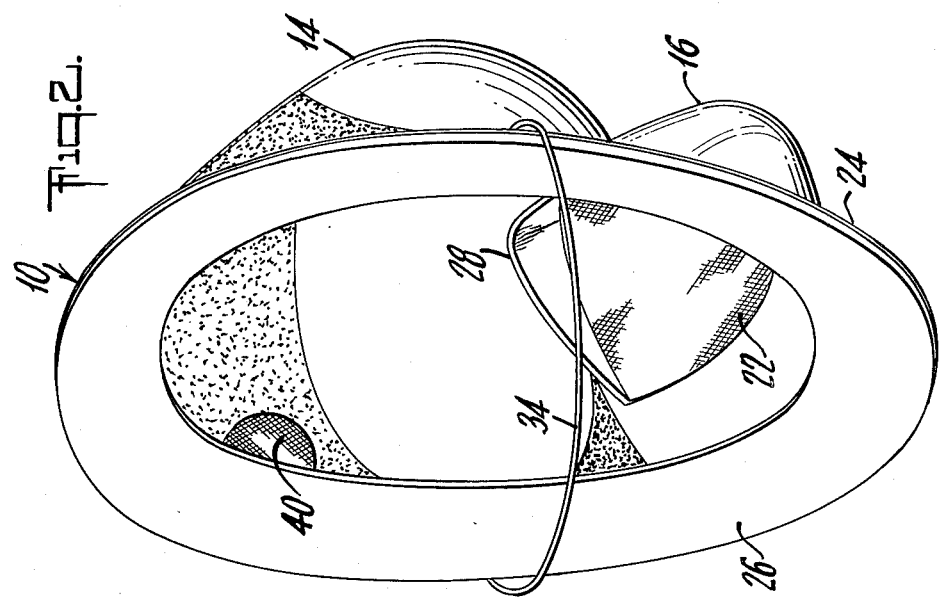
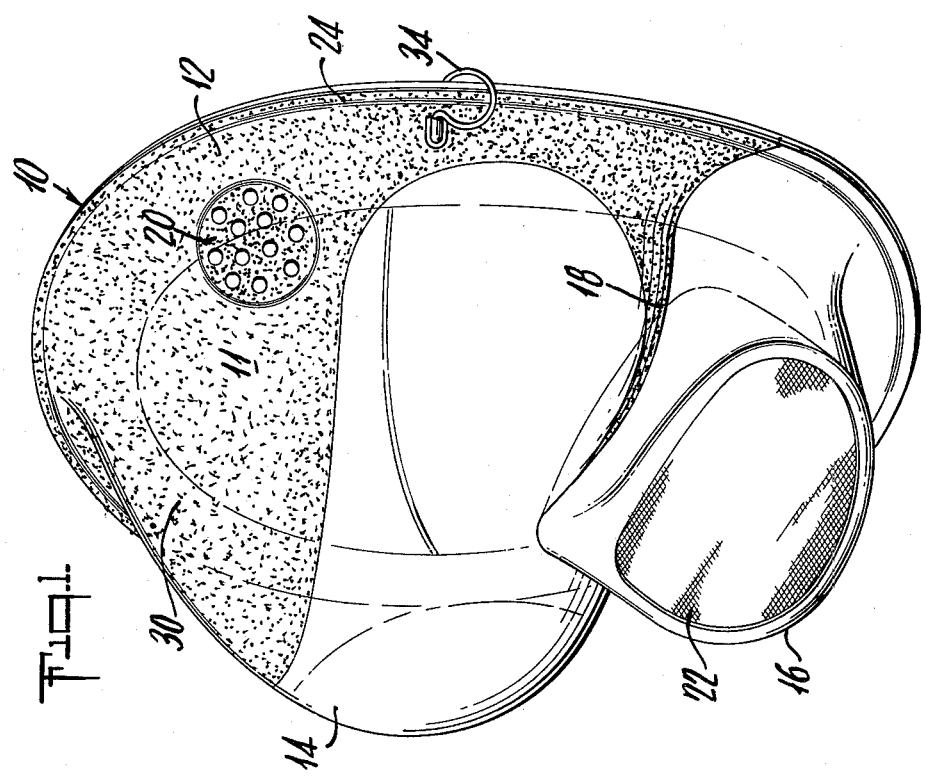

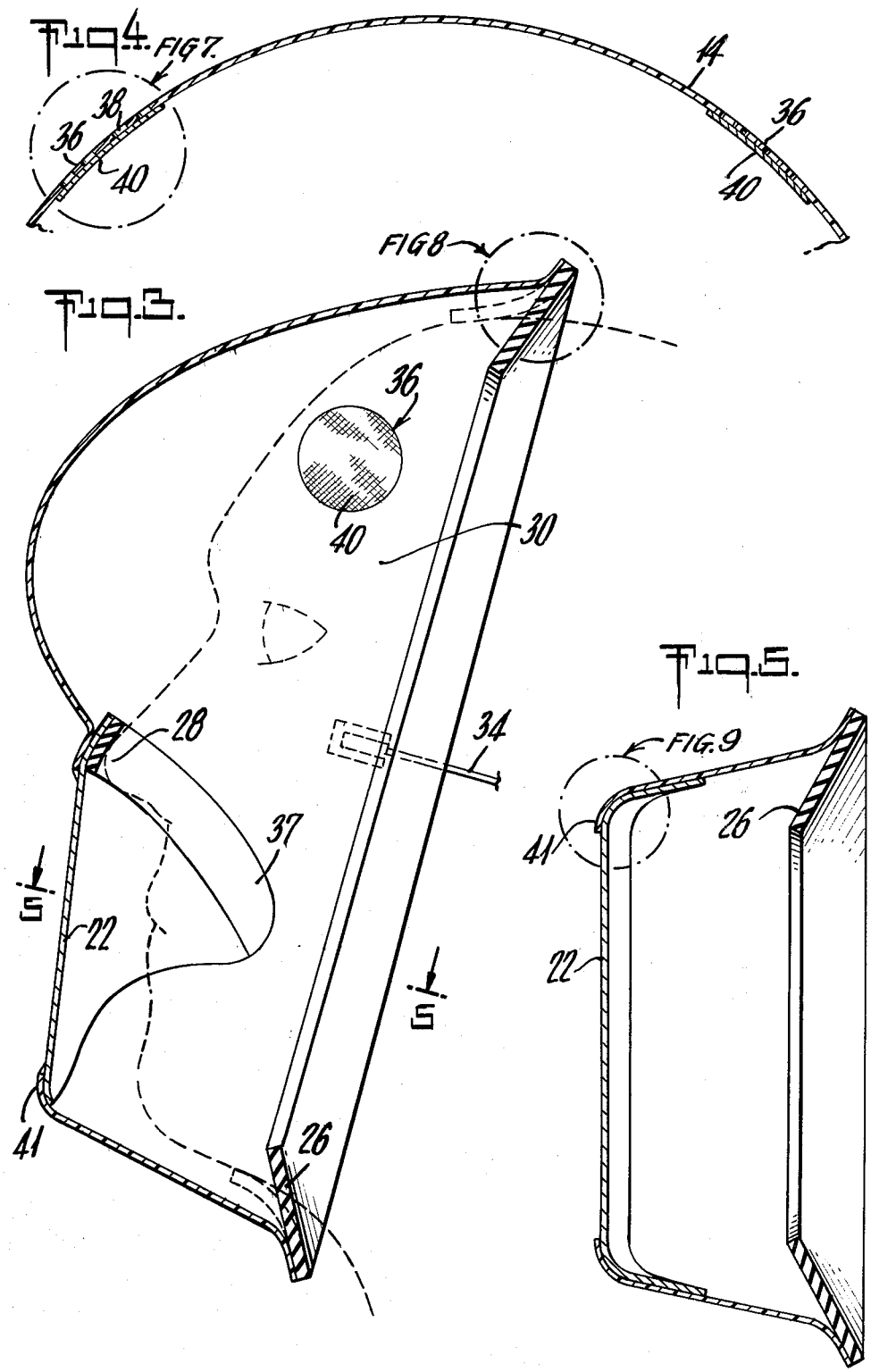

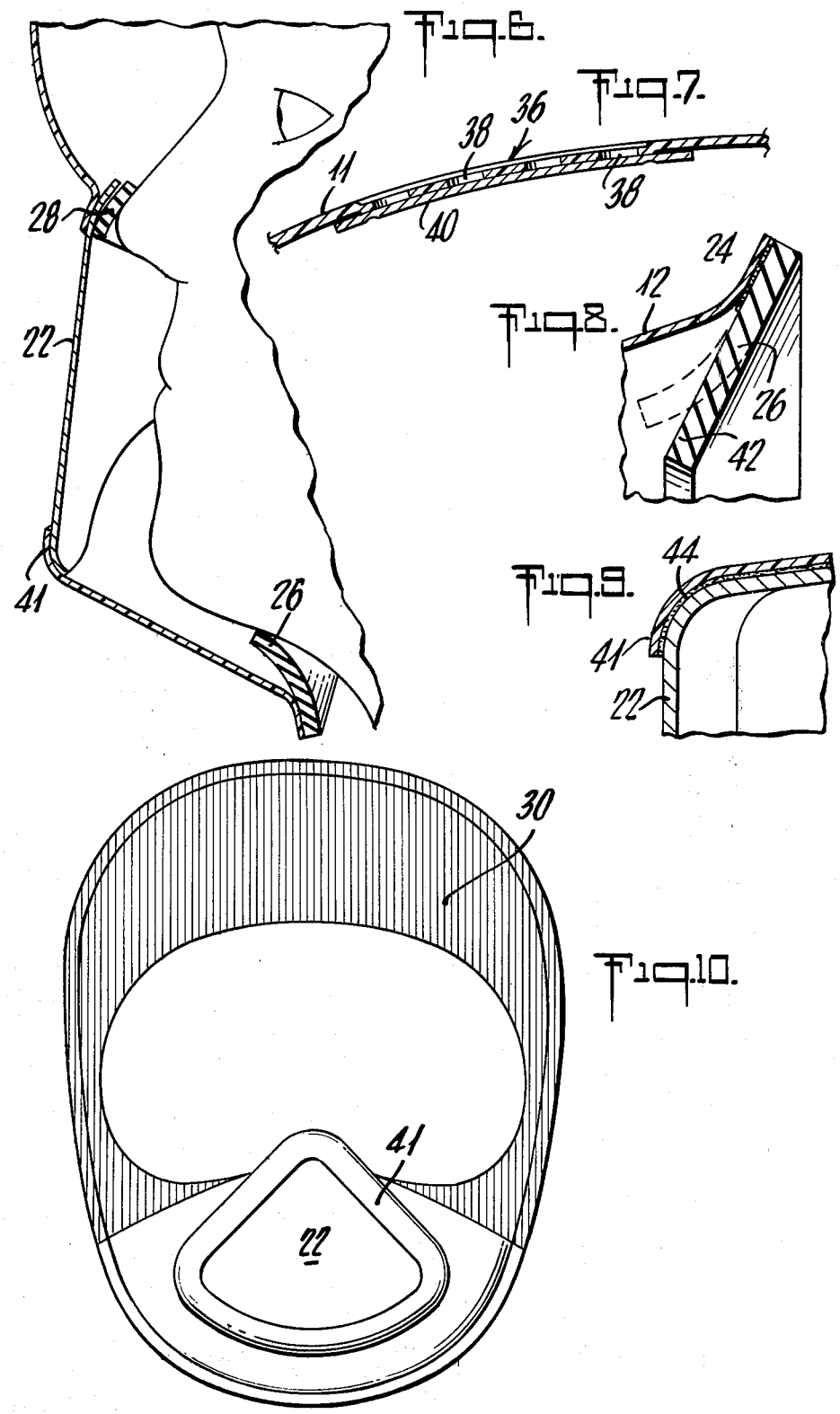

DISPOSABLE FULL-FACE SURGICAL MASK

BACKGROUND OF THE INVENTION

Face Masks have been developed for a variety of purposes including the protection of the face from cold or injury, the protection of the upper respiratory system of the wearer of the mask, and protection of others from infectious respiratory ailments of the wearer. Prior art face masks for these purposes, covering only the nose and mouth of the wearer, are disclosed in U.S. Pat. No. 3,249,108; Australian Patent No. 257,823; and United Kingdom Patent No. 1,239,039.

U.S. Pat. No. 4,126,131 discloses a goggle means or eye covering mask which is separate from but may be used in conjunction with a mask which covers the nose and mouth of the wearer.

U.S. Pat. No. 3,152,588 disclosess a face mask which covers the nose, mouth and eyes of the wearer but differs from the invention of the present application, for instance, in that the eye covering portion has a flat viewing surface, and in that it lacks means about the nose and cheeks for separating the upper and lower portions of the mask and creating two separate air compartments under the masks. In addition, the degree of contact of the face mask to the forehead and cheeks of the wearer would possibly subject him to claustrophobic effect.

Additional face mask constructions are disclosed in U.S. Pat. Nos. 4,029,092; 2,665,686; 1,313,745; and 3,768,100.

Traditionally, operating room personnel have been outfitted with fibrous or textile face masks which covered the mouth and nose of the wearer. Recently, there has been growing concern that such a face mask does not protect the patient from the shedding of skin cells from the faces of the operating room personnel, which skin cells may be the source of infection. Many techniques have been developed to give the operating room personnel full-face coverage. Most of these have involved a space-suit head covering with a diving-bell type of plastic mask held in place over the surgeon's head by a heavy frame. As the surgeon works in this attire he must step over and around the large hoses which draw air from around the face, under the mask, and through the hose to a compressor located outside the operating room. Each person on the operating team is so attired and attached to a separate hose leading out of the room. These plastic hoses and air compression means limit the mobility of the operating team.

In an alternative technique, the diving-bell type of mask construction is used in conjunction with a battery-powered portable air compressor strapped to the back of each member of the operating team. These compressors are connected to each person's mask through plastic tubes. However, the basic diving-bell type head cover is heavy and uncomfortable to the wearer, and is expensive to manufacture and use.

The present invention comprises a face mask which is lightweight, comfortable to wear, and disposable. When worn in combination with a surgical hood, the full face mask affects particulate containment of the entire head and face of the operating room personnel. The face mask also provides the wearer thereof with full face protection from possible contamination from their surroundings. In addition, the face mask can accommodate a miniaturized motor system for venting of the mask while worn, or may be used in combination with air compressors strapped to the body of the wearer, while avoiding the bulk and weight to the diving-bell type of mask.

SUMMARY OF THE PRESENT INVENTION

The present invention comprises a lightweight, disposable face mask for covering the entire face. The face mask comprises a unitary shell of transparent plastic material having an oval periphery, and upper and lower portions joined at a ridge which extends toward the face of the wearer. When the mask is worn the ridge traces the facial respiratory line, from about the tip of the nose to about the mid-point between the ear and mouth, above which the surface and contours of the face are subject to little movement during respiration. A bland of flexible or compressible material is disposed along the ridge of the shell and creates an aerodynamic seal to the varying facial contours of different wearers when the mask is worn. The aerodynamic seal created is exhaled air from contacting the upper portion. A soft, comfortable seal is formed between the face and mask by a strip of soft, flexible material which is secured to the rim of the periphery of the shell and extends inwardly of the periphery. The flexible strip at the periphery of the mask and the flexible or compressible band of material along the ridge permit the formation of the soft seal about the face and the aerodynamic seal along the facial respiratory line though the mask may be worn by people of varying head size and facial contours.

In a preferred embodiment of the mask, the rim of the periphery of the mask is disposed at a substantial angle to the periphery, and in a more preferred embodiment at an angle of from 90°–180°. The upper portion of the mask is provided with vent means to allow for air circulation and dissipation of heat and moisutre from under the upper portion of the mask when worn. Filter material may be disposed across the vent means to prevent particles from passing into or out of the face mask when worn.

The ridge, band, and vent means cooperate to substantially eliminate fogging of the upper portion. The upper portion has a generally bulbous configuration and is shaped so as to substantially eliminate parallax and distortion of vision of a wearer thereof. The vision of the wearer may also be enhanced by opaquing selected regions of the upper portion so as to reduce the glare from incident light when viewing through the remaining transparent regions.

The lower portion of the mask comprises a region of air filtration medium. In a still preferred embodiment, the air filtration medium is attached directly to the inside surface of the face mask and the band of compressible material is disposed along the ridge, over the air filtration medium.

The face mask of the present invention is comfortable to wear, inexpensive to manufacture, and is aesthetically very acceptable. When used as a surgical operating room mask, the face mask prevents contamination of a patient from skin cells shed from the face of operating room personnel. The potential for infecting the patient is further reduced when the face mask is worn in conjunction with a surgical hood. The face mask of the present invention also has utility in industrial and hobby applications such as painting, grinding, chipping and sandblasting, etc; in which applications the mask protects the eyes, face, and upper respiratory system of the wearer of the mask.

DESCRIPTION OF THE DRAWINGS

FIG. 1 is a perspective view of the front of a preferred embodiment of the face mask of the present invention.

FIG. 2 is a perspective view of the face mask of FIG. 1.

FIG. 3 is a cross-sectional view of the face mask of FIG. 1, shown in relation to the face of a wearer.

FIG. 4 is a cross-sectional view of the face mask shown in FIG. 3 taken along lines 4—4.

FIG. 5 is a cross-sectional view of the lower portion of the face mask of FIG. 3, taken along lines 5—5.

FIG. 6 is a partial cross-sectional view of the face mask of FIG. 1, shown in the configuration it assumes when disposed on the face of a wearer.

FIG. 7 is an expanded view of the air vent means illustrated in FIG. 4.

FIG. 8 is an expanded view of the rim of the periphery of the face mask and the strip of flexible material attached thereto as shown in FIG. 3.

FIG. 9 is an expanded view of the region of attachment of the air filtration medium and the side of the lower portion of the face mask as shown in FIG. 5.

FIG. 10 is a front view of another embodiment of the face mask of the present invention.

DETAILED DESCRIPTION OF THE INVENTION

The embodiment of the full face mask of the present invention illustrated in FIGS. 1 and 2 at 10, comprises a unitary shell 11 formed from a single piece of thin, transparent plastic polymer material. The shell may be either injection-molded or thermoformed in a manner known to one skilled in these arts. The shell has a generally oval periphery 12, and an upper portion 14 and a lower portion 16 separated by a ridge 18. The upper portion of the mask is of generally bulbous configuration and has been shaped to prevent distortion of the vision and parallax when worn. The upper portion has also been shaped to create a space sufficient between the mask and the face of the wearer thereof to accommodate the eyeglasses of the wearer. The upper portion of the mask has filter vent means 20, which can operate as air intake means in a motorized exhaust face mask and in an unmotorized face mask operates to dissipate heat and moisture of the upper portion of the mask when worn. The lower portion 16 of the mask has a region 22 thereof comprised of an air filtration medium. A rim 24 is formed at the periphery of the face mask and extends outwardly at the periphery at a substantial angle thereto. A strip 26 of flexible material is attached to the rim of the periphery and extends inwardly of the periphery of the mask. A band 28 of flexible or compressible material is disposed along the ridge separating the upper portion and the lower portion and forms an aerodynamic seal between the upper portion and the lower portion when the face mask is worn, which prevents fogging of the upper portion by warm air exhaled by the wearer. Selected regions 30 of the upper portion of the mask may be rendered opaque to eliminate possible glare in the lower end of 32 of the upper portion, which may be caused by intense lighting in the operating room. The band 28 may comprise either an open cell or a closed cell foam material or an integrally formed thin plastic flange 26. The strip 26 may also comprise an open or closed cell foam material or an integrally formed thin plastic flange and is preferably a closed cell foam.

FIG. 3 illustrates in cross-section one embodiment of the face mask of the present invention shown in relation to the face of the wearer thereof. It is necessary that the mask forms a particle seal with the face, requiring a line of contact between the mask and face about the entire periphery of the face, creating a potential claustrophobic effect on the wearer. When worn, the mask of the present invention floats on the face of the wearer, facial contact with the mask being limited to the band 28 and the flexed strip 26. Because of the angular orientation of the strip, the strip flexes when the mask is placed on the face of the wearer and only a small portion of the strip contacts the face of the wearer. By floating the mask on the flexed strip, fewer facial touch receptors are contacted by the mask reducing the claustrophobic potential and creating a mask which is comfortable and non-irritating to wear. The selected regions 30, which have been rendered opaque, lie outside of the field of vision of the wearer to retain peripheral vision of the wearer and to further reduce claustrophobic effect of the mask on the wearer thereof. In a preferred configuration shown in FIG. 3, the air filtration medium 22 is attached directly to the ridge 18 and the band of compressible material 28, disposed along the ridge is attached to the air filtration medium. When the mask is worn, the air filtration medium is preferably about $\frac{1}{2}''$ from the mouth and lips of the wearer for easier and clearer articulation,, and the cubic area enclosed by the lower portion approximates one quarter of the wearer's exhale volume or about 0.125 liters, to prevent $CO_2$ build-up. Means 34 for securing the face mask of the wearer are provided, and in this preferred embodiment, comprise an elastic band attached to the periphery of the mask.

FIG. 4 illustrates a cross-section of the vent means of FIG. 1 showing the vent means 36 disposed on opposed sides of the upper portion of the mask. The vent means, illustrated in expanded cross-section in FIG. 7, comprises perforations or openings 38 in the upper portion of the shell 11. Filtration means 40 is disposed along the under surface of the upper portion and is secured thereto so as to underlie the openings 38. Vent means 36 allow air circulation and the dissipation of heat and moisture generated under the upper portion of the face mask when worn. Filtration means 40 prevents particulate matter from entering or leaving the upper portion of the mask when worn. In an alternative construction, vent means 36 may comprise glare preventing louvered openings in the upper portion of the shell, with or without filtration means.

In the preferred embodiment illustrated in FIGS. 3 and 5, the filtration medium 22 not only comprises region 22 of the lower portion of the mask but extends along the inner surface of the lower portion of the ridge to the end points 37 of the band of flexible or compressible material. When constructing a mask of this configuration, it is possible to first attach the band of compressible material to the expanded piece of air filtration medium and then secure that composite along to the under surface of the mask at the ridge and along the edge 41 of the shell of the mask about region 22.

FIG. 6 illustrates a cross-section of the face mask, showing the band 28 of flexible or compressible material contacting the nose of the wearer, and further showing the strip 26 of soft, flexible material about the periphery of the mask as flexed when the mask is worn. The strip 26 forms a soft, comfortable seal between the periphery and the face of the wearer. When the mask is worn, the strip 26 flexes to form a soft seal with the face of the wearer allowing the mask to fit wearers of different face size and shape and rerducing the potential for claustrophobic effect of the mask on the wearer by minimizing the area of contact with the face. Preferably, the material of the strip 26 creates a particle barrier preventing facial skin cells of the wearer from escaping the mask. Open or closed cell foams may be used for this purpose provided they create a true particulate barrier. The band of flexible compressible material 28 contacts the nose and follows the facial respiratory line of the wearer which extends from the nose to a point approximately halfway between the ear and the corner of the mouth. The facial respiratory line separates the upper region of the face, which is subject to little movement during respiration, from the lower region of the face, the contours of which change during respiration and speech. The band 28 flexes or compresses to the relatively unchanging facial contours along the facial respiratory line creating an aerodynamic seal between the upper portion and the lower portion. The aerodynamic seal prevents fogging of the upper portion from warm air exhaled by the wearer. Open or closed cell foams may also be used as the flexible or compressible material provided they create an anti-fog seal between the upper and lower portions of the mask.

FIG. 8 illustrates an expanded cross-section of the attachment of the strip 26 of soft, flexible material to the rim 24 of the periphery 12. As shown, the rim extends outwardly of the periphery at a substantial angle to the periphery and is preferably at an angle between 90°-180° with respect to the periphery. In a still preferred configuration, the angle of the rim to the periphery is slightly layered about the lower portion than the upper portion to allow greater room to accommodate movement of the chin. The strip 26 of soft, flexible material is attached to the inside surface of the rim and extends inwardly of the periphery, creating a region 42 of the strip, which is free to flex to form a soft seal of minimum contact with the face of the wearer. In securing the air filtration medium to the edge of the shell about region 22, there is means of attachment or sealing that may be used including impulse, electric or ultrasonic sealing methods. In FIG. 9, the air filtration medium 22 is secured to at least the edge 41 of the shell by adhesive layer 44.

FIG. 10 illustrates a front view of a particular embodiment of the face mask of this invention illustrated in FIGS. 1 and 2 showing the selected regions 30 of the upper portion which have been rendered opaque. FIG. 10 also shows the edge 41 of the shell which surrounds the region 22 of air filtration medium.

The face mask of the present invention may be easily carried on top of the head prior to use and may be easily removed and replaced if necessary. The mask protects the face and upper respiratory system of the wearer, and is useful in medical, industrial and hobby applications. When used as an operating room surgical mask, it forms a barrier between the head and face of operating room personnel and the patient which not only filters out expired airborne bacteria but also effectively contains particulate matter such as sloughed off skin cells. A more complete and effective barrier between operating room personnel and the patient can be achieved when the face mask of the present invention is worn in conjunction with a surgical hood thereby completely encasing the head.

The foregoing description and the drawings are illustrative and are not to be taken as limiting. Still other variations and modifications are possible without departing from the spirit and scope of the present invention.

What is claimed is:

1. A comfortable, lightweight, disposable face mask for substantially, fully or completely covering the face and the front of the head of the wearer and having means for securing said face mask on the head of the wearer, said face mask comprising:

a unitary shell formed of a single piece of thin, transparent plastic material, said shell having an upper portion and a lower portion and having a generally oval periphery, said upper portion having a generally bulbous configuration and being large enough to accommodate the eyeglasses, if any, of the wearer, and being shaped so as to substantially prevent parallax and distortion of the vision, when the mask is worn, said lower portion, for covering the mouth and nose of the wearer, having a region thereof comprised of an air filtration medium;

said upper portion and said lower portion being joined along a shaped ridge which, when the mask is worn, projects toward the face of the wearer, said ridge having attached thereto a band which, when the mask is worn, contacts the nose and face of the wearer, thus substantially preventing breath exhaled by the wearer from reaching said upper portion of the mask;

said face mask having a strip of soft, flexible material attached to the entire periphery of the mask and extending inwardly of the periphery of the mask, said flexible strip and said band being the only portions of the mask which contact the face of the wearer when the mask is worn.

2. A face mask as in claim 1 wherein said upper portion further comprises vent means to dissipate heat and moisture generated under the upper portion of the mask when worn.

3. A face mask as in claim 2 wherein said vent means further comprises a filtration means to substantially prevent escape of particulate matter from under the upper portion of the mask when worn.

4. A face mask as in claim 2 wherein the vent means comprises two separate regions located on opposite sides of the upper portion of the face mask.

5. A face mask as in claim 1 wherein selected regions of the upper portion of the mask are rendered opaque to reduce glare from incident light.

6. A face mask as in claim 1 wherein when the mask is worn, the strip of flexible material forms a particulate seal to the face of the wearer of the mask.

7. A face mask as in claim 1 wherein the region thereof comprises of an air filtration medium is an effective bacterial filtration medium.

8. A face mask as in claim 1 wherein said air filtration medium is attached immediately to said ridge, and said band is disposed over said medium, along said ridge.

9. A comfortable, lightweight, disposable full face mask adapted to be worn without claustrophobic effect, said face mask comprising:

a shell having an upper portion and a lower portion and formed of transparent plastic material having a generally oval periphery having a rim extending outwardly of the periphery at a substantial angle to the periphery;

the upper portion of the mask having vent means to dissipate heat and moisture, said vent means including a filtration means to prevent escape of particulate matter through said vent means, the lower portion of the mask covering the mouth of the wearer and having a region comprising an air filtration medium which is an effective bacterial filtration medium, a strip of soft, flexible material fixed to said rim along the periphery and extending inwardly of said rim; and means for securing said face mask on the head of the wearer such that, when said mask is worn, said strip is hingedly flexed and lightly compressed against the head of a wearer with said shell covering the face of a wearer but positioned from a wearer's face.

10. A face mask as in claim 9 wherein the angle of said rim to said periphery is between 90°–180°.

11. The face mask of claim 9 wherein said strin is fixed to said rim around the entire periphery of the shell.

* * * * *